United States Patent [19]

Hodes et al.

[11] Patent Number: 4,513,083

[45] Date of Patent: Apr. 23, 1985

[54] PREPARATION OF AN ANTIBIOTIC SELECTIVELY EFFECTIVE AGAINST STAPHYLOCOCCUS INFECTIONS

[76] Inventors: David S. Hodes, Cricket La., Dobbs Ferry, N.Y. 10522; Grace Leidy; Katherine Sprunt, both of 21 Glenwood Ave., Leonia, N.J. 07605; Piper Weldy, 350 Bleeker St., New York, N.Y. 10014

[21] Appl. No.: 577,038

[22] Filed: Feb. 6, 1984

Related U.S. Application Data

[63] Continuation-in-part of Ser. No. 364,330, Apr. 1, 1982, abandoned.

[51] Int. Cl.[3] .......................... C12P 21/00; C12N 1/20; C12R 1/01
[52] U.S. Cl. .................................... 435/68; 435/253; 435/822; 424/115; 260/112 R
[58] Field of Search .................. 435/68, 253; 424/115, 424/177; 260/112 R

[56]  References Cited

PUBLICATIONS

Schleifer et al., Bacteriological Reviews, vol. 36 (4), pp. 407–477, (1972).

*Primary Examiner*—Lionel M. Shapiro
*Attorney, Agent, or Firm*—Hubbell, Cohen, Stiefel & Gross

[57] ABSTRACT

A strain (ATCC 31918) of *Rothia dentocariosa* which, upon fermentation, produces an antibiotic—staphylocidin—which is selectively effective against staphylococci, particularly those with *S. aureus* and *S. epidermidis;* and a process for producing such antibiotic by cultivation of the strain under aerobic conditions. Staphylocidin-containing products comprising the cell murein from the fermentation product are also disclosed.

13 Claims, 2 Drawing Figures

FIG. 2

EFFECT OF HOWLAND BROTH ON THE VIABILITY AND TURBIDITY OF STAPHYLOCOCCUS EPIDERMIDIS CULTURES

PREPARATION OF AN ANTIBIOTIC SELECTIVELY EFFECTIVE AGAINST STAPHYLOCOCCUS INFECTIONS

CROSS-REFERENCE TO RELATED APPLICATIONS

This application is a continuation-in-part of our copending application Ser. No. 364,330 filed Apr. 1, 1982, now abandoned.

TECHNICAL FIELD

This invention is directed to a strain of bacteria which, upon fermentation, produces an antibiotic selectively effective against staphylococcus, to an aerobic fermentation process utilizing such strain, and to fermentation products containing the antibiotic.

BACKGROUND ART

It has long been sought to develop narrow-spectrum antibiotics effective against particular pathogenic microorganisms but not against normal bacterial flora which apparently constitute one of the body's natural protective mechanisms against disease. Organisms which may be quite resistant to many known antibiotics and for which selective bactericides are needed include the staphylococci, e.g., *Staphylococcus aureus* and *Staphylococcus epidermidis*. These gram positive organisms have both been associated with wound and prosthesis infections, and *S. aureus* has also been implicated in a wide variety of systemic and localized diseases. While a number of broad spectrum antibiotics such as clindamycin, gentamicin, rifampin and methicillin are effective against these bacteria, no narrow spectrum antibiotics having selective antimicrobial activity against such staphylococcus infections have previously been developed.

It is, accordingly, among the objects of the present invention to provide a process for the preparaton of a narrow-spectrum antibiotic having selective antimicrobial activity against staphylococcus infections associated with *S. aureus* and S. epidermidis, and compositions containing that antibiotic. A further object of the invention is to provide such an antibiotic which is effective upon topical application, which leaves normal flora intact, and which because of its limited absorption obviates risk of systemic toxicity, particularly in the critically ill patient.

Other objects and advantages of the process and compositions of the invention will be apparent from consideration of the following detailed description of preferred embodiments thereof, considered in connection with the accompanying drawing.

BRIEF DESCRIPTION OF DRAWINGS

The details of our invention will be described in connection with the accompanying drawings, in which.

DISCLOSURE OF THE INVENTION

According to the present invention a new strain of the microorganism *Rothia dentocariosa* has been found. The new strain, hereinafter referred to as the Howland strain of *R. dentocariosa*, was recovered from a culture of the normal aerobic bacterial flora of a human pharynx. Upon aerobic fermentation the new strain produces a novel antibiotic substance, referred to herein as "staphylocidin", which has a narrow antibiotic spectrum and exhibits selective antimicrobial activity against staphylcocci including *S. auereus* and *S. epidermidis*.

A pure culture of the Howland strain has been deposited at the American Type Culture Collection, Rockville, Md., under its accession number ATCC 31918. A subculture of this living organism can be obtained upon request from the permanent collection of the ATCC.

It has been found that the Howland strain (ATCC 31918) produces staphylocidin upon fermentation in an aqueous nutrient medium containing assimilable sources of carbon, nitrogen and inorganic substances under submerged aerobic conditions. A staphylocidin-containing product comprising the cell walls or murein[1] produced during the fermentation is thereafter separated and recovered by a fractionation procedure known per se (Park, J. T., and Hancock, A., "A Fractionation Procedure for Studies of the Synthesis of Cellwall Mucopeptide and of other Polymers in Cells of *Staphylococcus aureus*", J. Gen. Micro. 22:249–258 [1960]).

[1] As previously recognized in the literature, cell murein is a peptidoglycan heteropolymer comprising glycan strands cross-linked through short peptides (Schleifer, K. H. and Kandler, O., "Peptidoglycan Types of Bacterial Cell Walls and their Taxonomic Implications", Bact. Rev. 36(4), pp. 407–477 [1972]).

Fermentation of the Howland strain to produce an antibiotic selectively effective against *S. aureus* and *S. epidermidis* was referred to in a paper by two of the present inventors, entitled "Antistaphylococcal Substance(s) from a Pharyngeal Organism", presented at a symposium of The American Pediatric Society and The Society for Pediatric Research on Apr. 29–May 2, 1970. The Howland strain was not identified in the paper and was not then deposited in any public culture collection, nor was the separation, recovery or characterization of the staphylocidin-containing cell murein fermentation product disclosed herein.

*R. dentocarisoa* has previously been identified, based upon the prototype strain deposited with the American Type Culture Collection, indexed as ATCC 17931. Based upon the typical peptidoglycan structure of cell mureins described by Schleifer, et al., supra, it is believed that murein prepared from the ATCC 17931 strain of *R. dentocariosa* ("ATCC murein" herein) has a polymeric structure incorporating the repeating units illustrated in Formula I below:

Formula I

As shown, the putative polymeric structure of ATCC murein thus incorporates a carbohydrate backbone comprising N-acetylglucosamine and N-acetylmuramic acid repeating units, a peptide unit, and an intrapeptide bridge connecting the peptide unit to another peptide unit.

The carbohydrate backbone in most bacteria similarly comprises alternating $\beta$-1,4-linked N-acetylglucosamine and N-acetylmuramic acid units as illustrated in Formula I. To date, only six variations have been described in the literature, and each such variation has occurred in the N-acetylmuramic acid residue (Ghuysen, J. M., Shockman, G. D., "Biosynthesis of Peptidoglycan", in "Bacterial Membranes and Walls", edited by Leive, L. New York: Marcel Dekker, Inc., p. 37 [1973]).

The structure of the cell murein produced by fermentation of the novel Howland strain of the present invention (herein the "Howland murein"), is, however, believed to differ from the ATCC murein both with respect to substitution of the N-acetylmuramic acid units in the carbohydrate backbone and in regard to the composition of the intrapeptide bridge units thereon. This hypothesis is predicated on the amino acid and amino sugar analyses of both the ATCC and Howland mureins described more fully below. Such analyses indicate that the ratio of muramic acid to glucosamine content of the Howland murein is about one third less than the ratio of such moieties in the ATCC murein, and that the Howland murein contains approximately one half the alanine content of the ATCC murein. The former fact suggests a difference in the structure of the carbohydrate backbones of the respective peptidoglycans, perhaps the further substitution of the N-acetylmuramic acid units of the Howland murein by a sugar having no amino groups thereon. The latter fact suggests structural differences in the intrapeptide bridge units of the respective macromolecules.

From the preceding it may be seen that the precise chemical structure of the Howland murein is not presently known. It may, however, otherwise be characterized, as indicated more fully below, as comprising a peptidoglycan polymer recovered from the fermentation product of the Howland strain, having a molecular weight at least equal to about 20 million Daltons, having the approximate amino acid and amino sugar content specified hereinafter, and incorporating the antibiotic material staphylocidin which is selectively effective against staphylococci including *S. aureus* and *S. epidermidis*.

Staphylocidin has not, prior to the present date, been structurally characterized. It is, however, believed that staphylocidin is an intrinsic part of the Howland murein macromolecule.

Evidence that staphylocidin is an integral part of the Howland murein polymeric structure is provided by reacting the Howland murein with various murolytic enzymes. Thus, on the one hand, when Howland murein is treated with any of the enzymes amylase, ribonuclease A, phospholipase A, chymotrypsin, pronase, or trypsin there is no charge in its antimicrobial activity. On the other hand, when treated with enzymes capable of digesting murein, e.g., lysozyme (which has N-acetylmuramidase activity), lysostaphin (which contains N-acetylglucosaminidase and N-acetylmuramyl-alanine amidase), or basidiomycetes lysing enzyme (which contains N-acetylmuramyl-alanine-amidase) the antimicrobial activity of the Howland murein is destroyed. The latter enzymes hydrolyze bonds between the sugar molecules of the carbohydrate backbone of Howland murein or the bond between the carbohydrate backbone and the peptide unit thereof. Based on these results it appears that the intact carbohydrate chain of Howland murein either comprises or is sterically essential to the activity of staphylocidin, and that the antibiotic is thus an integral part of the Howland murein macromolecule.

Moreover, bonding of staphylocidin to the Howland murein is suggested by gel filtration experiments in which Howland fermentation broths were passed through a Sephadex G-75 (a bead-formed, cross-linked dextran adsorbent gel commercially available from Pharmacia Inc.) column, and the active fraction was recovered from the column void volume, even after eluting with a high salt concentration solution (0.5M KCl), with 8M urea, or after boiling the broth samples in 1% sodium dodecyl sulfate and eluting the same with 0.1% sodium dodecyl sulfate. Since the gel column (which has a resolving range of 3,000–80,000 M.W. for globular proteins) did not separate the staphylocidin-containing fraction, it is postulated that the staphylocidin is covalently bound to the murein macromolecule.

BEST MODE FOR CARRYING OUT THE INVENTION

As indicated hereinabove, the antibiotic staphylocidin is produced by fermentation of a new strain (the Howland strain) of R. dentocariosa. The staphylocidin-containing fermentation product is obtained by isolation of the Howland murein and active fragments thereof (which may be present, inter alia, in the fermentation broth). The staphylocidin itself has not been separated from the Howland murein, but is believed to be covalently bonded to and part of the macromolecular structure thereof. Preferred embodiments of the novel microorganism and the process for cultivating the same to produce staphylocidin-containing products, data characterizing those products and documenting the selective antimicrobial activity thereof, and a description of the manner of use of products containing the antibiotic, are set out in detail below.

The Staphylocidin-Producing Bacterium

The Howland strain (ATCC 31918) has been identified as R. dentocariosa by the American Type Culture Collection, both on the basis of its morphology and its biochemical reactions. Thus, strains of R. dentocariosa are reported to be positive for catalase production, nitrate reduction, aesculin hydrolysis and acid production from glucose, maltose, mannose, melezitose, salicin, sucrose and trehalose (Bergey's Manual of Determinative Bacteriology, 8th Edition). After inoculation in brain heart infusion (Difco BHI) broth and growth for 48 hours at 37° C., the Howland strain is positive for each of these reactions. Similarly, the results from whole-cell hydrolysis and analysis of carbohydrate fermentation end products are also consistent with R. dentocariosa.

The Howland strain may further be characterized as follows:

(a) Morphology of colonies grown on BHI agar for 72 hours at 37° C.: colonies are smooth, creamy, off-white with an entire border, while the individual cells within each colony are gram-positive and cocco-bacillary in shape, do not incorporate any filamentous forms, and are not acid fast;

(b) Biochemical Reactions after growth for 48 hours at 37° C. as aforesaid (test results being determined 7 days after initiation of reaction):

|  | Positive (+) or Negative (−) Reaction |
| --- | --- |
| Hemolysis of sheep blood | − |
| Indole | − |
| Voges-Proskauer | − |
| Gelatinase | + |
| Nitrate reduction | + |
| Catalase | + |
| Urease | − |
| Lecithinase | − |
| Lipase | − |
| H$_2$S production | − |
| Hippurate hydrolysis | − |
| Aesulin hydrolysis | + |
| Starch hydrolysis | − |

(c) Acid-forming Reactions with:

|  | Positive (+) or Negative (−) Reaction |
| --- | --- |
| Adonitol | − |
| Amygdalin | − |
| L-Arabinose | − |
| Cellobiose | − |
| Dulcitol | − |
| Erythritol | − |
| D-Fructose | + |
| D-Galactose | − |
| D-Glucose | + |
| Glycerol | − |
| Glycogen | − |
| i-Inositol | − |
| Inulin | − |
| Lactose | − |
| Maltose | + |
| D-Mannitol | − |
| D-Mannose | + |
| D-Melezitose | + |
| Melibiose | − |
| Raffinose | − |
| L-Rhamnose | − |
| D-Ribose | − |
| Salicin | + |
| D-Sorbitol | − |
| L-Sorbose | − |
| Sucrose | + |
| Trehalose | + |
| D-Xylose | − |

(d) Whole-cell hydrolysate: galactose as the sole carbohydrate, no diaminopimelic acid and no arabinose; and (e) Carbohydrate fermentation end-products: lactic acid and succinic acid, but not propionic acid.

It will be understood that the morphology and biochemical reactions of the Howland strain may vary, depending upon the extent of growth of the culture upon examination or reaction. Thus, for example, cultures subjected to different growth conditions may include cells having filamentous as well as cocco-bacillary forms.

Process for the Preparation of the Staphylocidin-Containing Products

In accordance with this invention, the Howland strain, or a mutant thereof, is cultivated in an aqueous nutrient medium containing assimilable sources of carbohydrate, nitrogen and inorganic salts, under submerged aerobic conditions, until substantial antibacterial activity due to staphylocidin is produced.

The conditions of the fermentation for the biological conversion to staphylocidin are generally the same as utilized in presently known methods for producing various antibiotics by aerated submerged fermentation. The fermentation medium contains the usual nutrients and mineral substances. Suitable nutrients include any assimilable sources of carbon such as the polysaccharides or starches, or polyalcohols such as glycerol. An assimilable source of nitrogen may be supplied through the use of proteins, protein hydrolysates, urea, corn steep liquor, peptone, distillers solubles, fish meal and other conventional substances. The common anions and cations are supplied in the form of their non-toxic salts. Trace elements such as manganese, cobalt, zinc, copper, etc. are obtained either as impurities in the above compounds, through the use of tap water, or by specifically adding solutions especially enriched with these trace elements.

The other general conditions of the fermentation such as hydrogen ion concentration, temperature, time, rate of aeration, preparation of the inoculum, sterilization, inoculation and the like are conventional and are also similar to those utilized in the production of other antibiotics.

The fermentation is allowed to proceed under normal conditions for from about 24 to 72 hours, which is the period normally required to obtain good growth of the culture of the Howland strain. The antibiotic activity is thereafter recovered from the whole organism by procedures designed to purify murein, e.g., by the method of Park, et al., supra, involving harvesting of the whole cells, heating with trichloracetic acid, buffering and thereafter treating with trypsin. The Howland murein may be otherwise recovered by techniques known in the art, e.g., by treatment with trypsin, polyoxyethylene ethers (e.g., "Triton X-100"), and sodium dodecyl sulfate.

Particularly preferred examples of the process for fermentation of the Howland strain and recovery of the staphylocidin-containing Howland murein are described below:

EXAMPLE 1

Preparation of Staphylocidin by Fermentation in BHI Medium

The Howland strain was grown in a forced-air incubator in brain heart infusion broth (Difco BHI) at 35° C., with aeration by gentle shaking. After 65 hours of cultivation, the cells were harvested by centrifugation at 10,000 G for 30 minutes, and then washed three times with distilled water.

The cells were then suspended in 10% trichloracetic acid and heated to 95° C. for 20 minutes. The suspension was centrifuged at 10,000 G for 20 minutes and the resulting pellet was washed five times with 0.1M phosphate buffer having a pH of 7.0. The pellet was then re-suspended in phosphate buffer additionally containing 100 micrograms/ml trypsin, and the suspension incubated for two hours at 37° C.

The Howland murein thus recovered was thereafter washed four more times with distilled water. The resulting material was a white powdery material which, as indicated below, exhibited excellent antimicrobial activity against both S. aureus and S. epidermidis.

EXAMPLE 2

Preparation of Staphylocidin by Fermentation in Yeast Extract/Sucrose Medium

The Howland strain was incubated as in Example 1 with the exception that the cultivation was in a medium containing 4% of a commercial grade yeast extract (available from Yeast Products Co. as Ardamine Z) and 2% sucrose (available from Corn Products Co. as Cerelose) as the carbon source at pH 6.8. Recovery of the murein was as in Example 1.

Characterization of the Staphylocidin-containing Product

The Howand murein recovered as described hereinabove and having staphylocidin activity appears, as indicated hereinabove, to comprise a peptidoglycan macromolecule. The chemical structure of the Howland murein differs, however, from that of the ATCC murein, as evidenced in part by variations in the amino acid and amino sugar contents of the respective mureins.

Amino acid and amino sugar contents were determined by analysis in a microbore system employing an o-phthaldialdehyde fluorescence—high sensitivity detection system (Durrum) interfaced with a Perkin-Elmer data processor, integrator and microprocessor. The quantitative values of the amino acids and amino sugars were obtained by comparing the chromatograms of the two mureins with the chromatograms of authentic standards. The amino acid contents were determined after hydrolysis in 6N HCl at 110° C. in vacuo for 24 hours. The amino sugar analyses were conducted after mild acid hydrolyses (2N HCl at 100° C. for 2 hours).

The following comparative analyses were obtained:

TABLE I

COMPARATIVE AMINO ACID AND AMINO SUGAR CONTENTS OF HOWLAND AND ATCC MUREIN SAMPLES

| Amino Acid* | Howland Murein | ATCC Murein |
| --- | --- | --- |
| Asp | 0.16 | 0.07 |
| Thr | 0.09 | 0.05 |
| Ser | 0.07 | 0.04 |
| Glu | 0.43 | 0.35 |
| Gly | 0.16 | 0.09 |
| Ala | 1.00 | 1.00 |
| Val | 0.16 | 0.08 |
| Ile | 0.09 | 0.05 |
| Leu | 0.20 | 0.11 |
| Tyr | 0.06 | 0.03 |
| Phe | 0.08 | 0.04 |
| Lys | 0.34 | 0.29 |
| His | 0.04 | 0.02 |
| Arg | 0.10 | 0.05 |
| Muramic Acid | 0.47 | 0.63 |
| Glucosamine | 1.04 | 0.97 |

*Expressed Relative to Alanine: Amino Acids after 24 hr. hydrolysis, amino sugars after 2 hr. hydrolysis.

The Howland murein staphylocidin-containing product was further characterized and distinguished from the ATCC murein by thin layer chromatographic analysis. The analysis was carried out as follows:

200 mg of either Howland or ATCC murein was incubated with 10 mg lysozyme, 10 mg lysostaphin, 0.02% sodium azide, and 0.01M phosphate buffer, pH 7.0, for 48 hours in a 37° C. water bath. The murein digests were centrifuged at 10,000 G for 20 minutes and filtered with 0.45 micron filters. The filtrates were lyophilized and re-suspended in 0.5 ml distilled water.

Sephadex G-10 gel (a bead-formed, cross-linked dextran adsorbent gel commercially available from Pharmacia Inc.) was autoclaved and packed in a column in accordance with the manufacturer's directions. The column was run with sterile distilled water and forty 1-ml fractions were obtained. An assay for carbohydrate using the phenol/sulfuric acid method confirmed the presence of carbohydrates in the fractions. The fractions were thereafter lyophilized and dissolved in 50 ml of distilled water.

The several fractions, n-acetylmuramic acid and n-acetylglucosamine, were spotted on inactivated silica gel G plates and run in one dimension using iso-propanol/acetic/water 75:10:15 v/v/v. After drying, the plates were sprayed with 5% ammoniacal silver nitrate and heated at 100° C. for 10 minutes or until spots were obvious.

| *$R_f$ Value of Fraction | Howland Digest | ATCC Digest |
|---|---|---|
| | THIN LAYER CHROMATOGRAPHY OF SUGARS IN SEPHADEX G-10 FRACTIONS FROM ENZYME DIGEST OF ATCC AND HOWLAND MUREINS | |
| A | 0.66 ± 0.01 n-acetylglucosamine = 0.65 | 0.65 ± 0.01 n-acetylglucosamine = 0.62 |
| B | 0.58 ± 0.01 | 0.58 ± 0.01 |
| C | | 0.41 ± 0 |
| D | 0.59 ± 0.01 | 0.59 ± 0.01 |
| E | 0.74 ± 0.01 n-acetylmuramic acid = 0.73 | |

*$R_f$ is the ratio of the migration distance of the compound to the migration distance of the solvent.

The active principal of staphylocidin was further characterized as follows:

First, the Howland murein was suspended in glacial acetic acid at a concentration of 3.33 grams % (w/v), and the suspension was heated at 95° C. for 30 minutes. The solids were removed by centrifugation at 2,000×g, and the acetic acid thereafter removed from the supernatant liquid by evaporation under vacuum. The solid remaining after evaporation was a yellowish material which fluoresced green under long wave ultraviolet light using an ultraviolet visualizer, Raytech Model IS-88 (Raytech Industries, Stafford Springs, Conn.)

Alternatively, the murein was suspended in n-butanol at a 3.33 grams % concentration (w/v) and shaken for 15 minutes at room temperature. The solids were removed by centrifugation, and the butanol evaporated as above. Again, the solid remaining after evaporation was yellow-green and fluoresced green under long wave ultraviolet light.

The solid extracts produced by these techniques were sparingly soluble in aqueous solutions but were taken up in Dulbecco's phosphate-buffered saline (PBS) for antibiotic testing. They exhibited the same selective activity against *S. aureus* and *S. epidermidis*. Their antibiotic activities were similarly reduced 10-fold by dialysis using the 3,500 MW Spectropor dialysis membrane from Spectrum Medical Industries (Los Angeles, Calif.).

The solid extracts recovered from the Howland murein were further analyzed by the acetic acid and n-butanol techniques were further purified by thin-layer chromatography (TLC).

Both preparations were solubilized in n-butanol and chromatographed on 250 micron-thick microcrystalline cellulose plates (commercially available as "Avicel", from Analtech of Newark, Del.) with a methanol/acetic acid/PBS solvent system (75/10/15) resulting in identical chromatograms. Of three spots resolved, a single spot, migrating at $R_f$=0.98–0.99, contained all the antibiotic activity. This spot was unique in the chromatogram in that it fluoresced yellow-green in long wave ultraviolet light.

Yellow-green fluorescent spots with $R_f$ values of 0.04 on Avicel were detected when the chromatograms of the extracts were developed with either butanol/acetic acid/PBS (75/10/15) or ethyl acetate/pyridine/water (10/4/3).

When 250 micron-thick silica gel HL (Analtech) was employed as the solid phase, the $R_f$ values of the fluorescent spots resolved from the extracts in the methanol/acetic acid/PBS solvent system (75/10/15) were 0.88.

The fluorescent, biologically-active spot formed on an Avicel plate by TLC with the methanol/acetic acid/PBS system was removed from the plate, resolubilized in n-butanol, and applied to a SOTA C$_8$ high performance liquid chromatography (HPLC) column (SOTA, Crompond, N.Y.). The column was packed with a matrix consisting of particles having a 10 micron bead diameter with 332 Å pore diameters, the matrix having dimensions of 250×4.5 mm. The chromatogram was developed using a program directed by the Axxiom model 710 HPLC controller (Calabasas, Calif.). The pumps were Altex Model 110 A (Berkeley, Calif.), exerting a pressure of 1,000 psi. Integration and graphing were by a Spectra-Physics model SP 4270 integrator (San Jose, Calif.), and detection was by UV absorption at 280 nm (0.04 sensitivity) using a Kauer detector (Berlin, Germany). The flow rate was adjusted to 0.8 ml/min. The starting buffer was 0.035% trifluoroacetic acid (TFA) in H$_2$O. This was, in linear fashion, programmed to 90% of 0.035% TFA, 10% acetonitrile (AN) over 15 minutes. At this point the gradient was steepened to develop linearly a final buffer incorporating 95% AN and 5% of 0.035% TFA in 25 minutes.

The biologically active, butanol-solubilized, fluorescent spot gave a characteristic pattern in HPLC analysis with major peaks eluting at retention times of 3.25, 5.16, and 5.60 minutes and minor peaks, as indicated as in Table III below and as plotted in FIG. 1 of the accompanying drawings:

TABLE III

HPLC PEAKS FOR STAPHYLOCIDIN-CONTAINING EXTRACT

| Peak # | Area % | RT |
|---|---|---|
| 1 | 0.159 | 2.8 |
| 2 | 7.817 | 3.25 |
| 3 | 22.578 | 5.16 |
| 4 | 33.039 | 5.6 |
| 5 | 6.331 | 6.58 |
| 6 | 1.281 | 7.28 |
| 7 | 0.503 | 7.51 |
| 8 | 0.869 | 7.55 |
| 9 | 0.809 | 16.41 |
| 10 | 22.727 | 20.14 |
| 11 | 3.885 | 29.08 |
| Total | 100.--- | |

Antimicrobial Activity of the Staphylocidin-Containing Products

The antimicrobial spectrum of the Howland murein sample prepared as described in Example 1 above was determined, and compared with the spectrum of ATCC murein similarly produced. In the tests summarized in Table IV below, each test organism was inoculated in 1 ml of brain heart infusion, either with or without the addition of 5% sheep blood (depending upon the particular organism), and incubated overnight at 37° C. The antimicrobial concentrations of the Howland murein were determined as the number of micrograms of Howland murein per ml of Mueller Hinton agar containing 5% sheep blood at which less than five colonies of the particular test organism grew. As indicated below, the same concentrations of the ATCC murein had no antimicrobial effect.

TABLE IV
THE ANTIMICROBIAL SPECTRUM OF HOWLAND MUREIN AND ATCC MUREIN

| Organism | Number of Strains | Antimicrobial Concentration of Howland Murein | Antimicrobial Concentration of ATCC Murein |
|---|---|---|---|
| Listeria | 5 | NK[1] | NK[2] |
| B - Streptococcus A | 5 | NK | NK |
| B - Streptococcus B | 3 | NK | NK |
| Pneumococcus | 5 | NK | NK |
| Providencia | 5 | NK | NK |
| Serratia | 5 | NK | NK |
| Citrobacter diversus | 5 | NK | NK |
| Citrobacter freudii | 5 | NK | NK |
| Pseudomonas | 9 | 8-NK 1-2.1 μg/ml[2] | NK NK |
| Actinobacter | 5 | NK | NK |
| Shigella | 5 | NK | NK |
| Salmonella | 5 | NK | NK |
| Morganella | 5 | NK | NK |
| Staphylococcus epidermidis | 4 | 3-2.1 μg/ml[2] 1-33 μg/ml | NK NK |
| S. epidermidis* | 17* | 7-2.1 μg/ml 6-4.2 μg/ml 3-8.3 μg/ml 1-33 μg/ml | NK NK NK NK |
| Staphylococcus aureus | 10 | 1-2.1 μg/ml 6-4.2 μg/ml 1-8.3 μg/ml 2-NK | NK NK NK NK |
| S. aureus* | 12* | 6-2.1 μg/ml 5-4.2 μg/ml 1-8.3 μg/ml | NK NK NK |
| Enterobacter aerogenes | 5 | NK | NK |
| Enterobacter cloacae | 5 | NK | NK |
| Proteus rettgeri | 5 | NK | NK |
| Proteus mirabilis | 5 | NK | NK |
| Proteus vulgaris | 5 | NK | NK |
| Klebsiella pneumoniae | 10 | NK | NK |
| Escherichia coli | 10 | 9-NK 1-33 μg/ml[2] | NK |

The test organisms were diluted $10^{-2}$ in brain heart infusion with or without sheep blood, or in phosphate buffered saline at pH 7.4 where indicated by asterisk.
[1] $^*_2$ NK = No killing.
These numbers represent the number of strains killed at the antimicrobial concentration indicated.

Additional evidence of the selective antimicrobial effect of the staphylocidin-containing product against S. aureus was obtained by tests against cell-wall deficient cultures (L-forms) of S. aureus. The L-forms were induced in brain heart infusion agar containing 5% NaCl in 0.05M Tris HCl at pH 7.0, 20% horse serum, and 900 micrograms/ml of methicillin. Samples of the Howland broth (after 65 hours of cultivation) and the Howland and ATCC mureins prepared as described in Example 1 above (40 mg/ml) were similarly diluted 1:10 in 5% NaCl in 0.05M Tris HCl, pH 7.0.

The cell-wall deficient S. aureus test strain was streaked on agar plates. 20 microliters of the various test solutions (the pure buffer, and the Howland broth, Howland murein and ATCC murein prepared as described above) were then spotted on the agar plates. After 48 hours of incubation at 37° C., the clear area in the locality of each drop was rated semi-quantitatively from 1+ (low activity) to 4+ (high activity). As may be seen from Table V below, both the Howland broth and the Howland murein exhibited 4+ activity, whereas both the buffer and ATCC murein samples exhibited no activity:

TABLE V
THE ANTIMICROBIAL EFFECT OF HOWLAND AND ATCC STRAIN MUREINS ON CELL WALL DEFICIENT FORMS OF STAPHYLOCOCCUS AUREUS

| Sample | Activity |
|---|---|
| buffer | None |
| Howland broth | 4+ |
| Howland murein | 4+ |
| ATCC murein | None |

The antimicrobial effect of the staphylocidin-containing products of the invention against cultures of S. epidermidis has also been demonstrated. As indicated below, staphylocidin is both bactericidal and bacteriolytic for S. epidermidis.

In a first test an overnight culture of S. epidermidis was inoculated into BHI broth. A Howland broth, produced after 65 hours of fermentation as described in Example 1 above, and having an antimicrobial titer of 4+ at 1:100 dilution and 1+ at 1:400 dilution, was thereafter added to a first broth sample of the S. epidermidis culture after 4 hours growth thereof. A final dilution of S. epidermidis: Howland broth of about 1:10 was thus obtained in the first broth sample.

Figure 2:
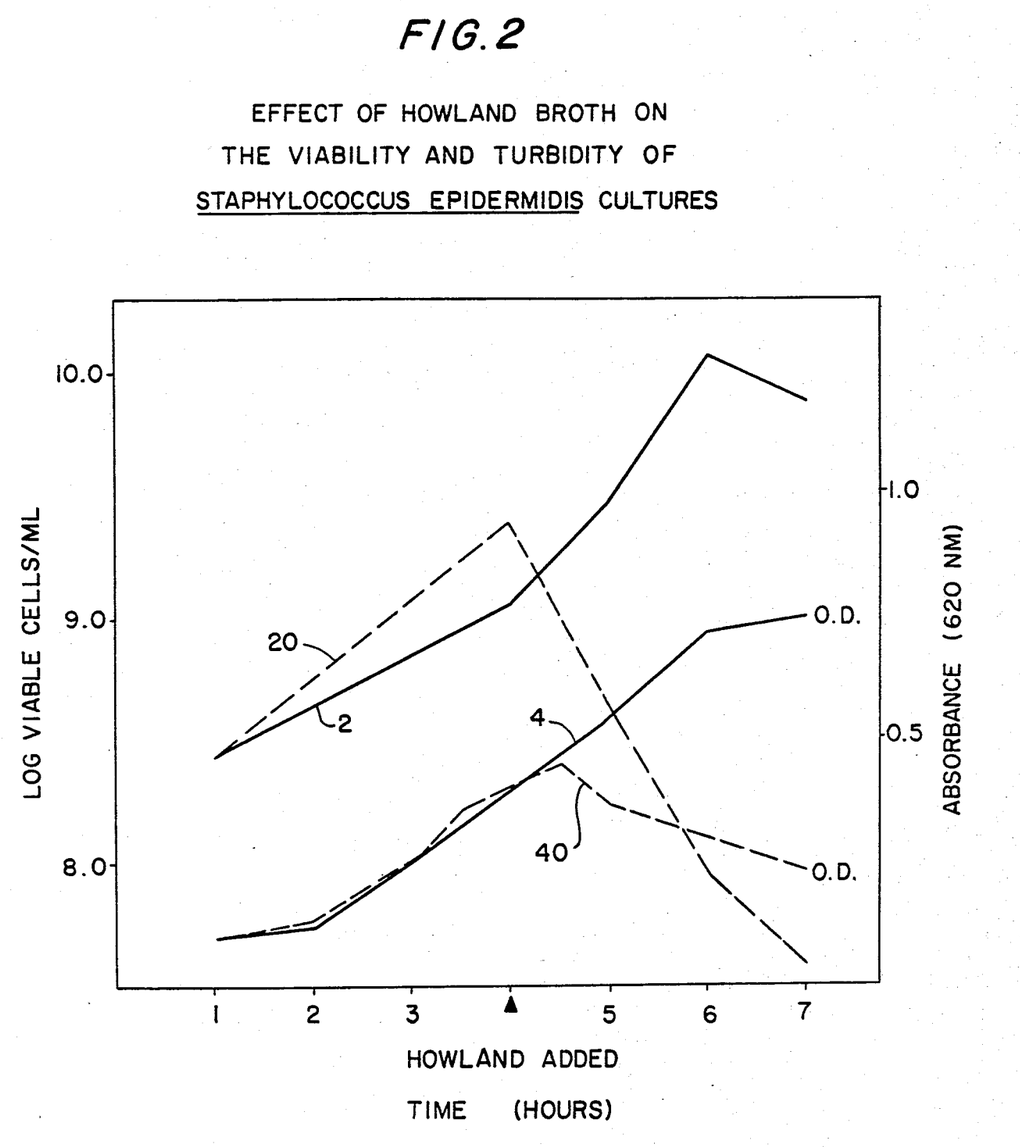
FIG. 2 is a graph illustrating the effect of staphylocidin on the viability and turbidity of an *S. epidermidis* culture.

The viable cell concentrations in the S. epidermidis broth sample (curve 2 in FIG. 2 of the accompanying drawing) and in the S. epidermidis: Howland broth sample (curve 20 in FIG. 2) were determined and plotted. Similarly, light absorbance (at 620 nm) was determined for both the S. epidermidis broth sample (curve 4 in FIG. 2) and the S. epidermidis: Howland broth sample (curve 40 in FIG. 2). The absorbance values illustrated in curve 40 were corrected for the optical effect of the Howland broth itself, curves 4 and 40 thus illustrating solely the decreased turbidity obtained upon lysis of the S. epidermidis by the staphylocidin-containing Howland broth. As may be seen in FIG. 2, both the viability and turbidity of the S. epidermidis culture was markedly decreased after inoculation with the Howland broth.

In a further test, the activity of the Howland murein was compared with the activity of the ATCC murein against the S. epidermidis strain. Various dilutions of the Howland and ATCC mureins were thus added to 1 ml of a broth suspension of the S. epidermidis strain. The samples were incubated at 35° C. for 3 hours, with vigorous shaking. As indicated in Table VI below, the addition of the ATCC murein was found competitively inhibit the anti-microbial activity of the Howland murein agaist S. epidermidis:

TABLE VI
EFFECT OF ATCC MUREIN ON THE ANTIMICROBIAL ACTIVITY OF HOWLAND MUREIN AGAINST S. EPIDERMIDIS

| Sample | Viable Colony-Forming Units/ml |
| --- | --- |
| Staph. | $1.1 \times 10^6$ |
| Staph. + 1:100 Howland murein | 0 |
| Staph. + 1:500 Howland murein | $1 \times 10^2$ |
| Staph. + 1:100 Howland + 1:10 ATCC murein | $7 \times 10^4$ |
| Staph. + 1:500 Howland + 1:10 ATCC murein | $3.5 \times 10^5$ |
| Staph. + 1:10 ATCC murein | $5.4 \times 10^5$ |

In preliminary in vivo tests with mice it has also been demonstrated that staphylocidin-containing fractions prepared in accordance with the present invention exhibit no apparent toxicity to the host animal. Thus, in a first test employing an autoclaved, undiluted broth supernatant from the fermentation of the Howland strain, no gross evidence of toxicity for 13–15 gram mice injected intraperitoneally with 0.5 ml of the test material twice within 24 hours was detected.

In a further experiment, it was shown that the cell murein recovered upon fermentation of a sub-population of the Howland strain exhibited activity against S. aureus in the immediate treatment of a mouse surgical-wound infection model, without inducing any acute toxic effects under the test conditions employed.

The staphylocidin-containing material was prepared from a rough phase sub-population of the Howland strain (deposited in the American Type Culture Collection under ATCC 31919). The rough phase colonies were dry, wrinkled, and crumbling with irregular edges, while the individual cells within each colony were gram-positive rods, pleomorphic, with diptheroid and coccal forms as well as many filamentous forms. The cells were not acid fast. The biochemical reactivity of the rough phase sub-population was similar to that of the total culture, differing only in that the rough phase gave a weak reaction in the Voges-Proskauer test, and produced acid on reaction with raffinose. The rough phase cell murein exhibited the same narrow, selective antimicrobial spectrum as the Howland murein, but only about 1/10 the antimicrobial activity thereof.

Utilizing the rough phase cell murein, activity significantly greater than a placebo material, but significantly lower than a gentamicin-containing topical formulation, was demonstrated in the mouse test.

Administration and Use of Staphylocidin-Containing Products

It is presently preferred that staphylocidin-containing formulations prepared as described herein be administered topically to prevent or treat local conditions commonly attributable to staphylococci or other susceptible organisms. When so applied topically, the active material is mixed with a suitable carrier such as a cream, gel or lotion. It is presently preferred to employ a gel-based carrier such, for example, as an acrylic acid polymer (e.g., that commercially available in 0.2% aqueous suspension as Carbopol 940 from B. F. Groodrich Corporation). In general, from about 1% to about 50% of the active material may be mixed with such a carrier to produce a suitable topical ointment. The methods for compounding, application, and administration of such topical formulations are well known in the art.

The mechanism of the antibacterial action of the preparations hereof against S. aureus and S. epidermidis is not currently known. However, (a) the data from murolytic enzyme digestion (demonstrating the importance of intact carbohydrate bonds for activity), (b) the fact that staphylocidin-containing products kill cell-wall deficient bacteria, and (c) the amino acid analyses showing differences in the carbohydrate backbones of active and inactive mureins, provide evidence of the possible biological mechanism. The steps in murein biosynthesis which do not involve reactions in the cell wall but do involve intact carbohydrate bonds occur in the lipid carrier cycle. It is possible that the murein components comprising staphylocidin irreversibly bind the lipid carrier molecule, preventing transfer of subunits from the cytoplasm into the cell membrane or from the membrane into the cell wall.

It will of course be understood that the present invention is in no way limited by the preceding hypothesis as to the possible reaction mechanism thereof.

The foregoing description of the preparation, use and application of the preferred forms of the process and compositions of the present invention is illustrative only, it being intended that the invention be limited only in accordance with the claims appended hereto.

We claim:

1. A biologically pure culture of the microorganism Rothia dentocariosa, having the identifying characteristics of ATCC 31918, said culture being capable of producing the antibiotic staphylocidin, having selective antimicrobial activity against staphylococci including S. aureus and S. epidermidis, in a recoverable quantity upon fermentation in an aqueous nutrient medium containing assimilable sources of carbon, nitrogen and inorganic substances.

2. The biologically pure culture of claim 1, characterized as follows:
(a) Morphology after 72 hours growth: colonies are smooth, creamy, off-white with an entire border, while the individual cells within each colony are gram-positive and cocco-bacillary in shape, and not incorporating any filamentous forms or being acid fast:
(b) Biochemical reactions after 48 hours growth:

|  | Positive (+) or Negative (−) Reaction |
| --- | --- |
| Hemolysis of sheep blood | − |
| Indole | − |
| Voges-Proskauer | − |
| Gelatinase | + |
| Nitrate reduction | + |
| Catalase | + |
| Urease | − |
| Lecithinase | − |
| Lipase | − |
| $H_2S$ production | − |
| Hippurate hydrolysis | − |
| Aesculin hydrolysis | + |
| Starch hydrolyis | − |

(c) Acid-forming reactions with:

|  | Positive (+) or Negative (−) Reaction |
| --- | --- |
| Adonitol | − |
| Amygdalin | − |
| L-Arabinose | − |
| Cellobiose | − |

-continued

| | Positive (+) or Negative (−) Reaction |
|---|---|
| Dulcitol | − |
| Erythritol | − |
| D-Fructose | + |
| D-Galactose | − |
| D-Glucose | + |
| Glycerol | − |
| Glycogen | − |
| i-Inositol | − |
| Inulin | − |
| Lactose | − |
| Maltose | + |
| D-Mannitol | − |
| D-Mannose | + |
| D-Melezitose | + |
| Melibiose | − |
| Raffinose | − |
| L-Rhamnose | − |
| D-Ribose | − |
| Salicin | + |
| D-Sorbitol | − |
| L-Sorbose | − |
| Sucrose | + |
| Trehalose | + |
| D-Xylose | − |

(d) Whole-cell hydrolyzate: galactose as the sole carbohydrate, no DAP and no arabinose; and (e) Carbohydrate fermentation end-products: lactic acid and succinic acid, but not propionic acid.

3. The biologically pure culture of claim 1, capable of producing upon fermentation a cell murein:

(a) comprising a peptidoglycan polymer having the following approximate amino acid and amino sugar contents:

| Amino Acid | Contents by Weight Relative to Alanine |
|---|---|
| Asp | 0.16 |
| Thr | 0.09 |
| Ser | 0.07 |
| Glu | 0.43 |
| Gly | 0.16 |
| Ala | 1.00 |
| Val | 0.16 |
| Ile | 0.09 |
| Leu | 0.20 |
| Tyr | 0.06 |
| Phe | 0.08 |
| Lys | 0.34 |
| His | 0.04 |
| Arg. | 0.10 |
| Muramic Acid | 0.47 |
| Glucosamine | 1.04; and |

(b) exhibiting the following $R_f$ values upon thin layer chromatography in an isopropanol/acetic acid/water system on silica gel G plates, after digestion with lysozymen and lysostaphin:

| Fraction | $R_f$ Value |
|---|---|
| (1) | 0.66 ± 0.01 |
| | [n-acetylglucosamine = 0.65] |
| (2) | 0.58 ± 0.01 |
| (3) | 0.59 ± 0.01 |
| (4) | 0.74 ± 0.01 |
| | [n-acetylmuramic acid = 0.73]; and |

Figure 1:
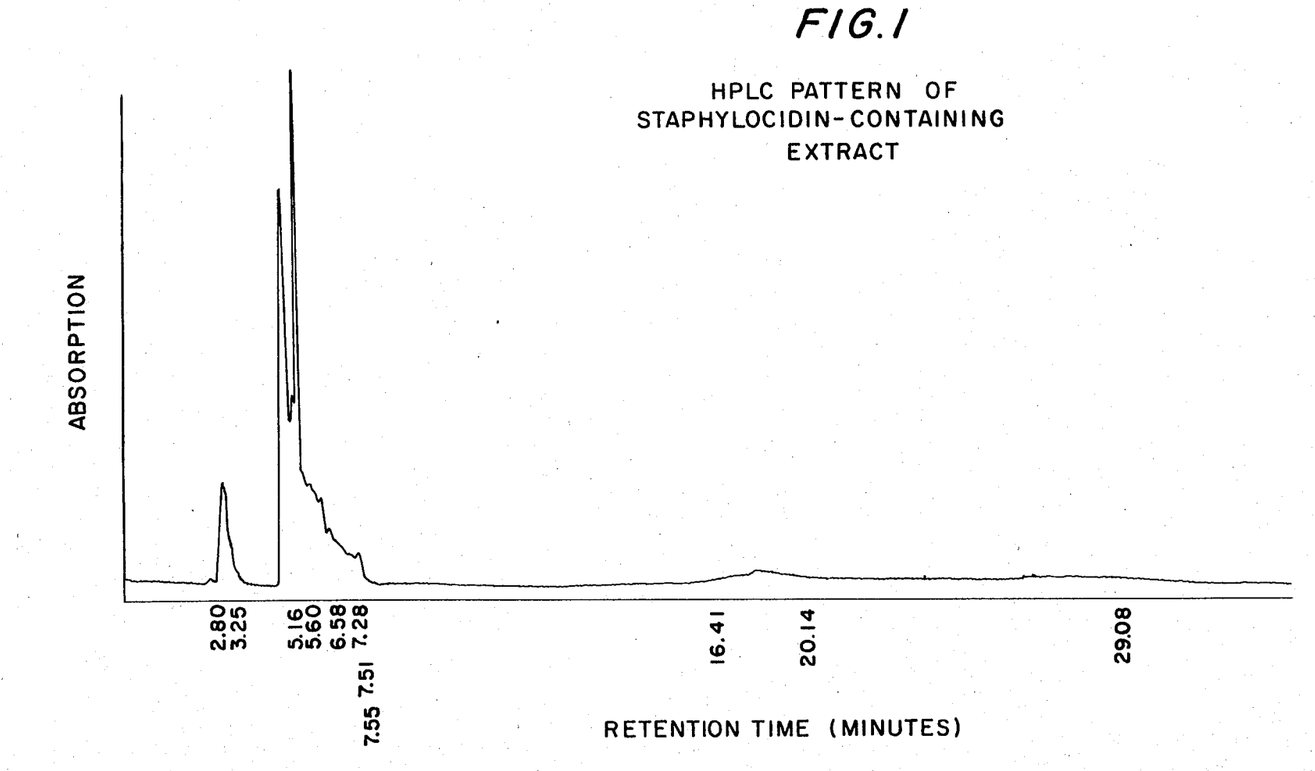
FIG. 1 is a plot of the values obtained upon high performance liquid chromatography (HPLC) of an extract containing the novel antibiotic of the invention.

(c) having bonded thereto the narrow-spectrum antibiotic staphylocidin, which is selectively effective against staphylococci including S. aureus and S. epidermidis;

the murein forming a staphylocidin-containing extract upon treatment with a glacial acetic acid or n-butanol solvent and evaporation of the solvent from the supernate, which extract exhibits the following characteristics:

(1) a biologically active component with an $R_f$ value of 0.98–0.99 upon thin layer chromatography in a methanol/acetic acid/phosphate-buffered saline system on a microcrystalline cellulose plate and yellow-green fluorescence in long wave ultraviolet light;

(2) a biologically active component with an $R_f$ value of 0.04 upon thin layer chromatography in a butanol/acetic acid/phosphate-buffered saline system on a microcrystalline cellulose plate and yellow-green fluorescence in long wave ultraviolet light;

(3) a biologically active component with an $R_f$ value of 0.04 upon thin layer chromatography in an ethyl acetate/pyridine/water system on a microcrystalline cellulose plate and yellow-green fluorescence in long wave ultraviolet light;

(4) a component with an $R_f$ value of 0.88 upon thin layer chromatography in a methanol/acetic acid/phosphate-buffered saline system on a silica gel plate and yellow-green fluorescence in long wave ultraviolet light; and (5) the $R_f$ 0.98–0.99 component containing staphylocidin and exhibiting the HPLC peaks plotted in FIG. 1 of the accompanying drawings.

4. A staphylocidin-containing product, which comprises the cell murein recovered from the fermentation product of the biologically pure culture of either of claims 1 or 2:

(a) comprising a peptidoglycan polymer having the following approximate amino acid and amino sugar contents:

| Amino Acid | Contents by Weight Relative to Alanine |
|---|---|
| Asp | 0.16 |
| Thr | 0.09 |
| Ser | 0.07 |
| Glu | 0.43 |
| Gly | 0.16 |
| Ala | 1.00 |
| Val | 0.16 |
| Ile | 0.09 |
| Leu | 0.20 |
| Tyr | 0.06 |
| Phe | 0.08 |
| Lys | 0.34 |
| His | 0.04 |
| Arg. | 0.10 |
| Muramic Acid | 0.47 |
| Glucosamine | 1.04; and |

(b) exhibiting the following $R_f$ values upon thin layer chromatography in an isopropanol/acetic acid/water system on silica gel G plates, after digestion with lysozymen and lysostaphin:

| Fraction | $R_f$ Value |
|---|---|
| (1) | 0.66 ± 0.01 |
| | [n-acetylglucosamine = 0.65] |
| (2) | 0.58 ± 0.01 |

| Fraction | R_f Value |
|---|---|
| (3) | 0.59 ± 0.01 |
| (4) | 0.74 ± 0.01 |
| | [n-acetylmuramic acid = 0.73]; and |

(c) having bonded thereto the narrow-spectrum antibiotic staphylocidin, which is selectively effective against staphylococci including S. aureus and S. epidermidis;

the murein forming a staphylocidin-containing extract upon treatment with a glacial acetic acid or n-butanol solvent and evaporation of the solvent from the supernate, which extract exhibits the following characteristics:

(1) a biologically active component with an R_f value of 0.98–0.99 upon thin layer chromatography in a methanol/acetic acid/phosphate-buffered saline system on a microcrystalline cellulose plate and yellow-green fluorescence in long wave ultraviolet light;

(2) a biologically active component with an R_f value of 0.04 upon thin layer chromatography in a butanol/acetic acid/phosphate-buffered saline system on a microcrystalline cellulose plate and yellow-green fluorescence in long wave ultraviolet light;

(3) a biologically active component with an R_f value of 0.04 upon thin layer chromatography in an ethyl acetate/pyridine/water system on a microcrystalline cellulose plate and yellow-green fluorescence in long wave ultraviolet light;

(4) a component with an R_f value of 0.88 upon thin layer chromatography in a methanol/acetic acid/phosphate-buffered saline system on a silica gel plate and yellow-green fluorescence in long wave ultraviolet light; and (5) the R_f 0.98–0.99 component containing staphylocidin and exhibiting the HPLC peaks plotted in FIG. 1 of the accompanying drawings.

5. A staphylocidin-containing product, which comprises the cell murein recovered from the fermentation product of the biologically pure culture of claim 3.

6. A process for producing the narrow-spectrum antibiotic staphylocidin having selective antimicrobial activity against staphylococci including S. aureus and S. epidermidis, which comprises cultivating the bacterium of claim 1 in an aqueous nutrient medium containing assimilable sources of carbon, nitrogen and inorganic salts under submerged aerobic conditions until substantial antibacterial activity due to staphylocidin is produced.

7. The process of claim 6, including recovering a staphylocidin-containing product by separating the cell murein having the staphylocidin bonded thereto from the fermentation broth.

8. A process for producing the narrow-spectrum antibiotic staphylocidin having selective antimicrobial activity against staphylococci including S. aureus and S. epidermidis, which comprises cultivating the bacterium of claim 2 in an aqueous nutrient medium containing assimilable sources of carbon, nitrogen and inorganic salts under submerged aerobic conditions until substantial antibacterial activity due to staphylocidin is produced.

9. The process of claim 8, including recovering a staphylocidin-containing product by separating the cell murein having the staphylocidin bonded thereto from the fermentation broth.

10. A process for producing the narrow-spectrum antibiotic staphylocidin having selective antimicrobial activity against staphylococci including S. aureus and S. epidermidis, which comprises cultivating the bacterium of claim 3 in an aqueous nutrient medium containing assimilable sources of carbon, nitrogen and inorganic salts under submerged aerobic conditions until substantial antibacterial activity due to staphylocidin is produced.

11. The process of claim 10, including recovering a staphylocidin-containing product by separating the cell murein having the staphylocidin bonded thereto from the fermentation broth.

12. A staphylocidin-containing product, prepared by the process of any of claims 6–11.

13. A product containing the narrow spectrum antibiotic staphylocidin which is selectively effective against staphylococci including S. aureus and S. epidermidis, said product comprising a peptidoglycan polymer obtained from the microorganism Rothia dentocariosa, having the identifying characteristics of ATCC 31918, said polymer having the following approximate amino acid and amino sugar contents:

| Amino Acid | Contents by Weight Relative to Alanine |
|---|---|
| Asp | 0.16 |
| Thr | 0.09 |
| Ser | 0.07 |
| Glu | 0.43 |
| Gly | 0.16 |
| Ala | 1.00 |
| Val | 0.16 |
| Ile | 0.09 |
| Leu | 0.20 |
| Tyr | 0.06 |
| Phe | 0.08 |
| Lys | 0.34 |
| His | 0.04 |
| Arg | 0.10 |
| Muramic Acid | 0.47 |
| Glucosamine | 1.04 | and which product:

(a) exhibits the following R_f values upon thin layer chromatography in an isopropanol/acetic acid/water system on silica gel G plates, after digestion with lysozyme and lysostaphin:

| Fraction | R_f Value |
|---|---|
| (1) | 0.66 ± 0.01 |
| | [n-acetylglucosamine = 0.65] |
| (2) | 0.58 ± 0.01 |
| (3) | 0.59 ± 0.01 |
| (4) | 0.74 ± 0.01 |
| | [n-acetylmuramic acid = 0.73]; and |

(b) is so bonded to the staphylocidin as to be non-dissociable therefrom after treatment with 8 molar urea or boiling with sodium dodecyl sulfate;

(c) upon treatment with a glacial acetic acid or n-butanol solvent and evaporation of the solvent from the supernate, leaves a staphylocidin-containing extract exhibiting the following characteristics:

(1) a biologically active component with an R_f value of 0.98–0.99 upon thin layer chromatography in a methanol/acetic acid/phosphate-buffered saline system on a microcrystalline cellulose plate and yellow-green fluorescence in long wave ultraviolet light;
(2) a biologically active component with an $R_f$ value of 0.04 upon thin layer chromatography in a butanol/acetic acid/phosphate-buffered saline system on a microcrystalline cellulose plate and yellow-green fluorescence in long wave ultraviolet light;
(3) a biologically active component with an $R_f$ value of 0.4 upon thin layer chromatography in an ethyl acetate/pyridine/water system on a microcrystalline cellulose plate and yellow-green fluorescence in long wave ultraviolet light; and
(4) a component with an $R_f$ value of 0.88 upon thin layer chromatography in a methanol/acetic acid/phosphate-buffered saline system on a silica gel plate and yellow-green fluorescence in long wave ultraviolet light;
(5) the $R_f$ 0.98–0.99 component containing staphylocidin and exhibiting the HPLC peaks plotted in FIG. 1 of the accompanying drawings.

* * * * *